United States Patent [19]

Webb

[11] Patent Number: 5,367,072
[45] Date of Patent: Nov. 22, 1994

[54] REAGENTS FOR AUTOMATED SYNTHESIS OF PEPTIDE ANALOGS

[75] Inventor: Thomas R. Webb, Encinitas, Calif.

[73] Assignee: Corvas International, Inc., San Diego, Calif.

[21] Appl. No.: 807,474

[22] Filed: Dec. 13, 1991

Related U.S. Application Data

[63] Continuation-in-part of Ser. No. 627,753, Dec. 14, 1990, Pat. No. 5,283,293.

[51] Int. Cl.$^5$ ............................................ C07D 225/00
[52] U.S. Cl. .................................... 540/483; 540/610; 546/332; 548/567; 562/507; 562/560
[58] Field of Search ................ 562/507, 560; 540/483, 540/610; 546/332; 548/567

[56] References Cited

PUBLICATIONS

CA 113(2):11940j, "Polyamino–Acid Derivative-Containing U.V. Absorbent . . . ", Nakayama et al., 13 Oct. 1989.

*Primary Examiner*—Bernard Lipman
*Attorney, Agent, or Firm*—Lyon & Lyon

[57] ABSTRACT

Reagents suitable for synthesis of peptide analogs using automated peptide synthesis and procedures for synthesis of peptide analogs are provided.

14 Claims, 5 Drawing Sheets

REAGENTS FOR AUTOMATED SYNTHESIS OF PEPTIDE ANALOGS

CROSS-REFERENCE TO RELATED APPLICATIONS

This application is a continuation-in-part of U.S. Ser. No. 07/627,753, filed Dec. 14, 1990, now U.S. Pat. No. 5,283,293, the disclosure of which is incorporated herein by reference.

FIELD OF THE INVENTION

This invention relates to methods for the automated solid-phase synthesis of peptide analogs and to novel reagents useful therein. In one aspect, the present invention is directed to a process which uses novel reagents which comprise novel heterobifunctional semicarbazide (I), or semicarbazone (II) or (III) linker moieties which may be attached to insoluble resins (or supports), via a pendant carboxylic acid group to give a support reagent suitable for automated solid phase synthesis of peptide analogs. The resulting support reagent is suitable for use in a conventional automated or semi-automated peptide synthesizer using protected amino acids or amino acid analogs, to give a protected peptide (or peptide analog) aldehyde, attached to the support reagent. The product peptide aldehyde or peptide analog is cleaved from the support and deprotected to give the desired peptide analog in good yield. Using this process and reagents of the present invention, peptide aldehydes and analogs can be rapidly and efficiently produced. These peptide analogs are useful as enzyme inhibitors and have potential as pharmaceutical agents.

BACKGROUND OF THE INVENTION

Analogs which utilize the catalytic mechanism of an enzyme (e.g. transition-state inhibitors) have been suggested as enzyme inhibitors, however it has only been recently that this idea has been explored. A major problem has been the difficulty in synthesizing the target peptide analog molecules. One candidate group are analogs having the aldehyde group. These peptide analogs are particularly attractive in that they can be prepared from naturally occurring amino acids. Highly specific and potent peptide transition-state analog enzyme inhibitors would be of interest as therapeutic agents. Solution methods for the synthesis of peptide aldehydes have been developed, however, their preparation remains a tedious, labor intensive, and time consuming process. The development of a methodology for the automated synthesis of these aldehyde derivatives will allow for the rapid synthesis of a large number of these analogs and, thus, would facilitate the exploration of enzyme inhibition structure-activity relationships. The availability of such analogs would facilitate the development of drugs that selectively inhibit specific serine or cysteine proteinases.

The serine proteinases may be suitable targets for inhibition by peptide transition-state analogs. The trypsin sub-family is composed of serine proteinases which hydrolyse peptide bonds that follow an arginine or lysine residue. Trypsin-like enzymes play a physiological role in digestion, coagulation, fibrinolysis, blood pressure regulation, fertility, and inflammation (see: "Design of Enzyme Inhibitors as Drugs" Eds. Sandler, M., Smith, H. J., Oxford Science Publications, 1989). Selective inhibitors of members of this family of enzymes may therefore be useful in the intervention of many disease states. The catalytic mechanism of serine proteinases involves the attack of the active-site serine on the carbonyl bearing the sissile amide bond of the substrate, to give a tetrahedral intermediate. It has been reported that peptide analogs which are stable mimics of this tetrahedral intermediate (i.e., transition-state analogs) can be selective enzyme inhibitors (see Delbaere, L. T. J., Brayer, G. D., J. Mol. Biol. 183:89–103, 1985 and Aoyagi, T., Umezawa, H., Eds., Proteases and Biological Control, Cold Spring Harbor Laboratory Press, 429–454, 1975). Methods for identifying potent and selective inhibitors (as potential drugs) is an active area of research.

Peptide aldehydes were initially discovered as natural products produced by a number of actinomycete strains. Some of these derivatives have bee reported to be selective inhibitors of various types of serine and cysteine proteinases (see Aoyagi, T. et al., cited above). For example, the peptide alaninal elastatinal is a potent elastase inhibitor, while not inhibiting trypsin or trypsin-like enzymes (see Hassall, C. H. et al., FEBS Lett., 183:201–5, 1985). In several cases, the selectivity of these naturally occurring analogs has been enhanced by modifying the sequence. (See, e.g., Bajusz, S. et al., J. Med. Chem. 33:1729–1735, 1990, and McConnell, R. M. et al., J. Med. Chem. 33:86–93, 1990.) Elastase inhibitors are of interest in the treatment of diseases such an emphysema and synthetic peptide aldehydes have been reported to be excellent inhibitors of human leucocyte elastase (see "Design of Enzyme Inhibitors as Drugs" cited above). The peptide arginal leupeptin has been reported to be a selective inhibitor of trypsin-like enzymes (see Aoyagi, T., Umezawa, H., Eds., "Structures and activities of protease inhibitors of microbial origin", Proteases and Biological Control, Cold Spring Harbor Laboratory Press, 429–454, 1975). Leupeptin, along with naturally occurring variants and synthetic analogs, has been reported to be potent inhibitors of several trypsin like enzymes in the coagulation cascade. Synthetic peptide analogs have been prepared which are reported to show a marked selectivity for particular coagulation factors. For example, one such analog (Me-D-Phe-Pro-Arg-al) has been developed as a thrombin inhibitor and is reported to have significant in vivo anticoagulant activity. (See U.S. Pat. Nos. 4,316,889 (1982), 4,399,065 (1983), 4,478,745 (1984), 4,346,078 (1982), and 4,708,039 (1987).)

Resins for the affinity isolation of specific enzymes have been reported which have unprotected peptide and amino acid aldehydes attached to insoluble supports. (See Patel et al., Biochem, Biophys. Res. Comm. 104, 181–186 (1982) and Patel et al., Biochem. Biophys. Acta, 748, 321–330 (1983).) Those resins were neither intended nor suitable for use in the solid phase synthesis of peptide aldehydes, since the support was attached to the N-terminus of the peptide aldehyde.

Methods for the solution synthesis of peptide aldehydes have been reported. See, e.g., McConnell et al. and references therein; and Bajusz, S. et al. both cited above; Kawamura et al., Chem, Pharm. Bull., 17: 1902 (1969), and Someno et al., Chem. Pharm. Bull. 34, 1748, (1986). The use of semicarbazides as aldehyde protecting reagents for the solution synthesis of peptide aldehydes has also been reported. Westerik and Wolfnden, J. Biol. Chem., 247, 8195 (1972), Ito et al., Chem. Pharm. Bull. 23, 3081, (1975), and McConnell et al. (cited above). The use of a soluble semicarbazide functionalized polymer has been reported for the manual preparation of some peptide aldehydes. Galpin et al., (Pept. Struct. Funct. Proc. Am Pept. Symp., 9th, 799–802 (1985). Edited by: Deber, C. M., Hruby, V. J., Kopple, K. D., Pierce Chem. Co.: Rockford, Ill.). However, such supports were not suitable for the automatic synthesis of peptide aldehydes, since they dissolve in the solvents used for the coupling steps.

SUMMARY OF THE INVENTION

The present invention relates to methods for the automated synthesis of peptide analogs and for reagents useful for such methods. Such syntheses can be performed on conventional automated peptide synthesizers, using the novel solid insoluble support reagents (hereafter referred to as "semicarbazone (or semicarbazide) amino acid aldehyde supports" or "SAAA supports") of the present invention. The present invention also relates to novel linker moieties used to prepare the SAAA supports. These linker moieties have the general structure:

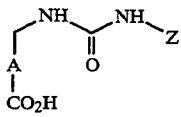

wherein
(a) A is a divalent spacer group which comprises a non-reactive divalent hydrocarbyl group having from 2 to about 15 carbon atoms; and
(b) Z is (i) —NH—Pr;  (I)

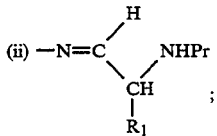  (II)

or

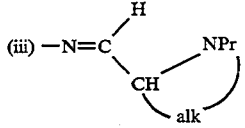  (III)

wherein Pr is a protecting group removable under non-adverse conditions; $R_1$ is hydrogen, or alkyl of 1 to 12 carbon atoms, cycloalkyl of 5 to 8 carbon atoms, aryl or aralkyl of about 7 to about 15 carbon atoms, all optionally substituted with 1 to 3 groups independently selected from hydroxy, sulfhydryl, alkylthio, carboxyl, amide, amine, alkylamine, idolyl, 3-N-formylindolyl, benzyloxy, halobenzyloxy, guanido, nitroguanido or imidazolyl optionally substituted with alkoxyalkyl; alk is an alkylene group of about 3 to about 12 carbon atoms optionally substituted with 1 to 3 substituents independently selected from hydroxy, alkyl, aryl or guanido and provided that any functional groups of $R_1$ or alk which are reactive under conditions of peptide synthesis are optionally protected by a protecting group which is removable under non-adverse conditions.

Suitable protecting groups, Pr, include t-butoxycarbonyl (BOC), 9-fluorenylmethyloxycarbonyl (FMOC) and other suitable protecting groups.

Suitable non-reactive hydrocarbyl groups, A, are those which are substantially inert (and may have suitably protected functional groups) under conditions for automated and semi-automated peptide synthesis. Preferably A has from about 5 to about 10 carbon atoms. A is preferably a divalent $C_5-C_8$ cycloalkylene group optionally substituted with 1 to about 5 alkyl groups such as a 1,4-cyclohexylene group, or a divalent $C_5-C_8$ arylene or aralkylene group optionally substituted with 1 to about 5 alkyl groups such as a 1,3- or 1,4-phenylene radical, an alkyl-1,3- or 1,4-phenylene radical or the like.

Preferably $R_1$ is hydrogen, or a protected or unprotected amino acid side chain. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, histidine, phenylalanine, tyrosine, and tryptophan. Preferred alk groups include propylene to give the side chain of the amino acid proline. Where the amino acid side chain contains functional groups which are reactive under conditions for peptide synthesis, those groups are preferably protected by suitable protecting groups which are removable under non-adverse conditions. Other suitable $R_1$ or alk groups include the side chains of the following amino acids: hydroxyproline, norleucine, 3-phosphoserine, homoserine, O-phosphohomoserine, dihydroxyphenylalanine, 5-hydroxytryptophan, 1-methylhistidine, 3-methylhistidine, and β-aspartyl phosphate. Other naturally occurring amino acid metabolites or precursors having side chains which are suitable for use as $R_1$ groups herein include α-amino-adipic acid, cysteine sulfonic acid, cysteic acid and ornithine. As noted above, preferred alk groups include propylene, optionally substituted with hydroxy to give a proline or hydroxyproline analog.

In the SAAA supports (or "support reagents") of the present invention, the carbon of the C-terminal carboxyl group is attached to a solid support or resin or such that the hydroxy group of the C-terminal carboxyl group is replaced by —X wherein —X is independently selected from —NH—sp, —O—Sp, and —CH$_2$—Sp, wherein Sp denotes an insoluble support, preferably a suitably functionalized 1% cross-linked polystyrene.

The support reagents of the present invention are conveniently prepared using protecting groups suitable for chemically extending the peptide chain by conventional automated solid phase techniques. Such protecting groups include, but are not limited to t-butoxycarbonyl (BOC) and 9-fluorenylmethyloxycarbonyl (FMOC), allyloxycarbonyl and the like. See for example, Green, T.; "Protecting Groups in Organic Synthesis," (John Wiley and Sons, 1981). For a general description of peptide synthesis, see Greenstein, J. P., Winitz, M. "Chemistry of the Amino Acids," pages 763–1268. (John Wiley and Sons: New York, 1986).

Once the peptide transition state analog has been extended on the SAAA support to give the desired sequence and chain length, the analog can be cleaved from the support by mild acid/formaldehyde treatment. The protecting groups on the N-terminus and sidechains of the amino acid components of the analog are selected so that they are not affected by cleavage of the peptide analog from the support. If desired, acid or base sensitive protecting groups can be removed before cleavage. A deprotection step involving catalytic hydrogenation after cleavage of the peptide analog from the support may be used, since many protecting groups (e.g., benzyl, benzyloxycarbonyl, benzyloxymethyl, halobenzyloxycarbonyl, and nitor) are readily removed by mild hydrogenolysis without affecting functionality of the desired final product (see, e.g., Example 8).

In another aspect, the present invention is directed to peptide analogs of the formula:

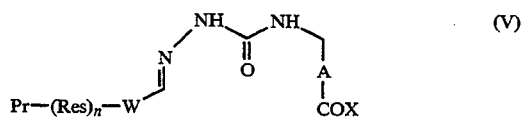 (V)

wherein Pr is a protecting group removable under non-adverse conditions, Res is an independently selected amino acid residue, n is an integer greater than zero, W is

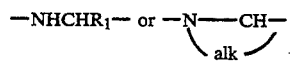

wherein $R_1$ is hydrogen; or alkyl, cycloalkyl, aryl or aralkyl, optionally substituted with 1 to 3 substituents independently selected from hydroxy, alkoxy, sulfhydryl, alkythio, carboxyl, amide, amino, alkylamino, indolyl, 3-N-forylindolyl, benzyloxy, halobenzyloxy, guanido, nitro-guanido- or optionally substituted imidazolyl substituted with alkoxy-alkyl; and alk is an alkylene group of about 3 to about 12 carbon atoms optionally substituted with 1 to 3 substituents independently selected from hydroxy, alkyl, aryl or guanido; A is a non-reactive hydrocarbyl group of 2 to about 15 carbon atoms; and X is independently —NH—Sp, O—Sp, or —CH$_2$—Sp, where Sp is an insoluble resin support; and provided that any functional groups of Res, $R_1$ or alk which are reactive under conditions of peptide synthesis are optionally protected by a protecting group which is removable under non-adverse conditions, which are conveniently prepared using the linker moieties and support reagents of the present invention.

Preferred A groups are those having 5 to 10 carbon atoms. More preferably, A is a divalent $C_5$–$C_8$ cycloalkylene group, a $C_5$–$C_8$ divalent arylene group or a $C_5$–$C_8$ divalent aralkylene group, all optionally substituted with 1 to 5 alkyl groups. Especially preferred A groups include 1,3-cyclohexylene, 1,4-cyclohexylene, 1,3-phenylene, 1,4-phenylene, 1,3-xylylene, 1,4-xylylene and the like.

Preferred $R_1$ and alk groups are those which correspond to the side chains of the amino acids typically found in proteins, i.e., glycine, alanine, valine, leucine, isoleucine, serine, threonine, cysteine, methionine, glutamic acid, aspartic acid, glutamate, aspartate, lysine, arginine, histidine, phenylalanine, tyrosine, tryptophan and proline. Also preferred are amino acid residues, Res, having $R_1$ or alk groups which comprise those amino acid side chains.

Preferred are those compounds wherein n is less than 10 (to give a decamer after cleavage) or more preferably less than 5 (to give a pentamer).

An additional aspect of the present invention is directed to methods of preparing the above peptide analog (V) using the linker moieties and support moieties of the present invention. After cleavage and deprotection, a peptide aldehyde of the formula H—(—Res—)$_n$—W—CHO (VI)

is obtained, wherein Res and W are as defined in conjunction with formula V after removal of any protecting groups. These methods are particularly suitable for preparing peptide analogs where n is less than 10 (a decamer) or less than 5 (a pentamer).

Definitions

As used herein, the following terms have the following meanings, unless expressly stated to the contrary:

The nomenclature used to define the peptides is that specified by Schroder & Lubke, "The Peptides," Academic Press (1965), wherein in accordance with conventional representation the amino group at the N-terminus appears to the left and the carboxyl group at the C-terminus to the right.

The term "amino acid residue" refers to radicals having the structure (i) —C(O)RNH— wherein R typically is —CH($R_1$)— and $R_1$ is H or a carbon containing substituent, or (ii)

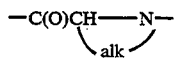

wherein alk is an alkylene group. For the most part, the amino acids used in the application of this invention are those naturally occurring amino acids found in proteins, or the naturally occurring anabolic or catabolic products of such amino acids which contain amino and carboxyl groups. Also included are the D and L stereoisomers of such amino acids when the structure of the amino acid admits of stereoisomeric forms. For the purposes of this application, unless expressly noted to the contrary, a named amino acid shall be construed to include both the D or L stereoisomers, preferably the L stereoisomer.

The term "hydrocarbyl" denotes an organic radical composed of carbon and hydrogen which may be aliphatic (including alkyl, alkenyl, and alkynyl groups and groups which have a mixture of saturated and unsaturated bonds), alicyclic (carbocyclic), aryl (aromatic) or combinations thereof; and may refer to straight-chained, branched-chain, or cyclic structures or to radicals having a combination thereof, as well as to radicals substituted with halogen atom(s) or heteroatoms, such as nitrogen, oxygen and sulfur and their functional groups (such as amino, alkoxy, aryloxy, carboxyl, ester, amide, carbamate or lactone groups, and the like), which are commonly found in organic compounds and radicals.

The term "hydrocarbylcarbonyl" refers to the group

wherein R' is a hydrocarbyl group.

The term "alkyl" refers to saturated aliphatic groups, including straight, branched and carbocyclic groups.

The term "aryl" refers to aromatic hydrocarbyl and heteoaromatic groups which have at least one aromatic ring.

The term "aralkyl" refers to an alkyl group which has been substituted with an aromatic (or aryl) group, and includes, for example, groups such as benzyl.

The term "alkylene" refers to straight and branched-chain alkylene groups which are biradicals, and includes, for example, groups such as ethylene, propylene, 2-methylpropylene (e.g.

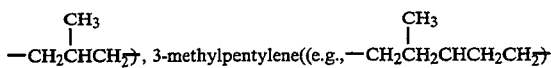

and the like.

The term "arylene" refers to aromatic groups which are biradicals.

The term "aralkylene" refers to aralykyl groups which are biradicals.

The term "ester" refers to a group having a

linkage, and includes both acyl ester groups and carbonate ester groups.

The term "halo" or "halogen" refers to fluorine, chlorine, bromine and iodine.

The term "non-adverse conditions" describes conditions of reaction or synthesis which do not substantially adversely affect the skeleton of the peptide analog and/or its amino acid (and/or amino acid analog) components. One skilled in the art can readily identify functionalities, coupling procedures, deprotection procedures and cleavage conditions which meet these criteria.

The term "support" refers to a solid particulate, insoluble material to which a linker moiety of the present invention is linked and from which a peptide analog may be synthesized. Supports used in synthesizing peptide analogs are typically substantially inert and nonreactive with the reagents used in the synthesis of peptide analogs and include resins such as that included in the SAAA support reagents of the present invention.

The term "peptide analog" refers oligomers of amino acids (or amino acid residues) which are linked by peptide linkages wherein either the C-terminal carboxyl or the N-terminal amino has been chemically modified to another functional group or replaced with a different functional group. For example the C-terminal carboxyl group may be replaced with an aldehyde group.

The term "automated synthesis" or "automated peptide synthesis" refers to the synthesis of peptides or peptide analogs using an instrument which carries out the individual steps of each addition cycle to add a amino acid or amino acid analog to the growing peptide chain occurs without manual manipulation.

The term "semi-automated synthesis" or semi-automated peptide synthesis refers to the synthesis of peptides or peptide analogs where in each addition cycle to add an amino acid or amino acid analog to a growing peptide chain, the coupling step is done manually and other individual steps occur without manual manipulation. Thus, semi-automated synthesis differs from automated synthesis in that some of the coupling steps are carried out manually.

DETAILED DESCRIPTION OF THE INVENTION

Figure 1A:
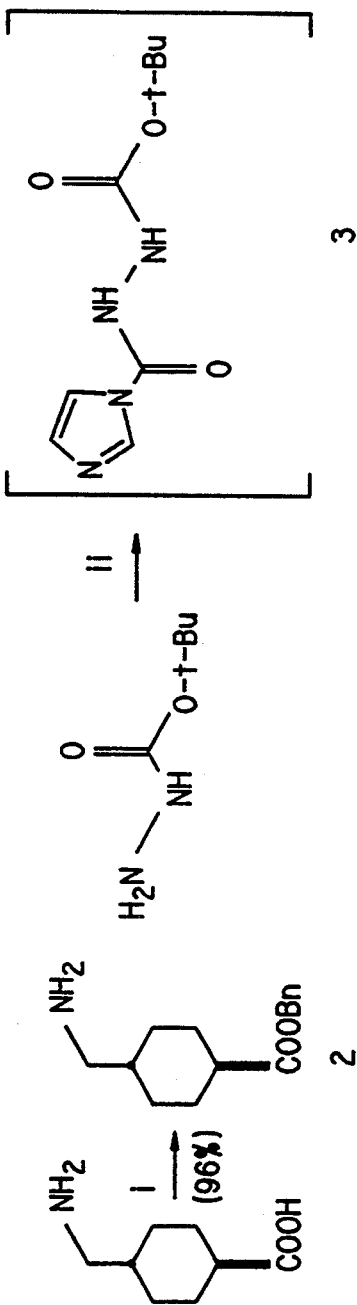
FIG. 1 depicts general reaction schemes for the preparation of certain some reagents according to the present invention.

Accordingly, aspects of the present invention are directed to processes for the synthesis of support reagents which comprise novel linker moieties and the peptide analogs derived therefrom, as well as processes whereby transition-state peptide analogs are prepared using said support reagents.

A. Peptide Synthesis

Techniques for solid-phase peptide synthesis are described in "Solid-Phase Peptide Synthesis," Steward & Young, (Freeman & Co., San Francisco, 1969) and U.S. Pat. No. 4,105,603, issued Aug. 8, 1978. Classical solution synthesis methods are described in detail in the treatise "Methoden der Organischen Chemie-(Houben-Weyl) Synthese von Peptiden," E. Wunsch (ed.) (1974), (Georg Thieme Verlag, Stuttgart, W. Ger). The fragment condensation method of synthesis is described in U.S. Pat. No. 3,972,859 issued Aug. 3, 1976; other synthesis methods are described by U.S. Pat. No. 3,842,067 issued Oct. 15, 1974 and U.S. Pat. No. 3,862,925 issued Jan. 28, 1975, the disclosures of which are incorporated herein by reference.

The peptide chain of the peptide analog to be synthesized may be extended using solid-phase synthesis methods, such as that generally described by Merrifield, J. Am. Chem. Soc. 85:2149 (1963); however other chemical syntheses protocols known in the art may be used. Solid-base synthesis is initiated from the C-terminus of the peptide aldehyde or analog to be synthesized by coupling a protected $\alpha$-amino acid to a suitable SAAA support. Examples of supports or resins which are suitable for the preparation of SAAA supports of the present invention include MBHA, BHA, aminomethyl phenyl resins and the like. The preparation of the hydroxymethyl resin is described by Bodansky et al., Chem. Ind. 38:1597-1598 (London) 1966. Chloromethylated resins are commercially available from BioRad Laboratories, Richmond, Calif. and from Lab. Systems, Inc. The preparation of resins is described by Stewart et al., "Solid Phase Peptide Synthesis," Chapter 1, pages 1-6 (Freeman & Co., San Francisco 1969). BHA and MBHA resin supports are commercially available, but have conventionally been used only when the desired polypeptide being synthesized has an unsubstituted amide at the C-terminus.

The peptide chain is extended by coupling additional amino acids to the chain using known techniques for the formation of peptide bonds. One suitable method comprises converting the $\alpha$-amino protected amino acid to be added to the peptide chain to an "activated" derivative wherein the carboxyl group is rendered more susceptible to reaction with the free N-terminal $\alpha$-amino group of the peptide fragment. For example, the amino acid can be converted to a mixed anhydride by reaction of a protected amino acid with ethyl chloroformate, pivaloyl chloride or like acid chlorides. Alternatively, the amino acid can be converted to an active ester such as a 2,4,5-trichlropheyl ester, a pentachlorophenol ester, a pentafluorophenyl ester, a p-nitrophenyl ester, a N-hydroxysuccinimide ester, or an ester formed from 1-hydroxybenzotriazole.

Another coupling method involves use of a suitable coupling agent such as N,N'-dicyclohexylcarbodiimide or N,N'diisopropylcarbodiimide. Other appropriate coupling agents are disclosed in E. Gross & J. Meinenhofer, *The Peptides: Analysis, Structure, Biology*, Vol. I: Major Methods of Peptide Bond Formation (Academic Press, New York, 1979).

The α-amino groups of amino acids (monomers) employed in the peptide synthesis are protected during the coupling reaction to prevent side reactions involving the reactive, if unprotected, α-amino function. In addition, certain amino acids contain reactive side-chain functional groups (e.g., sulfhydryl, amino, carboxyl, and hydroxyl) which must also be protected with suitable protecting groups to prevent chemical reaction of those groups from occurring during both the initial and subsequent coupling steps. Suitable protecting groups, known in the art, are described in E. Gross & J. Meienhofer, *The Peptides: Analysis, Structure, Biology*, Vol. 3: Protection of Functional Groups in Peptide Synthesis (Academic Press, New York, 1981).

In selecting a particular side-chain protecting group to be used during synthesis of the peptide analogs, the following considerations may be determinative. An α-amino protecting group (a) should render the α-amino function inert under the conditions employed in the coupling reaction, (b) should be readily removable after the coupling reaction under conditions that will not remove side-chain protecting groups and will not alter the structure of the peptide fragment, and (c) should eliminate the possibility of racemization upon activation immediately prior to coupling. An amino acid side-chain protecting group (a) should render the side chain functional group inert under the conditions employed in the coupling reaction, (b) should be stable under the conditions employed in removing the α-amino protecting group, and (c) should be readily removable upon completion of the desired amino acid peptide aldehyde under reaction conditions that will not alter the structure of the peptide analog chain.

It will be apparent to those skilled in the art that the protecting groups known to be useful for peptide synthesis will vary in reactivity with the agents employed for their removal. For example, certain protecting groups such as triphenylmethyl and 2-(p-biphenylyl)isopropyloxycarbonyl are very labile and can be cleaved under mild acid conditions. Other protecting groups, such as t-butyloxycarbonyl (BOC), t-amyloxycarbonyl, adamantyloxycarbonyl, and p-methoxybenzyloxycarbonyl are less labile and require moderately strong acids, such as trifluoroacetic, hydrochloric, or boron trifluoride in acetic acid, for their removal. Still other protecting groups, such as benzyloxycarbonyl (CBZ), halobenzyloxycarbonyl, p-nitrobenzyloxycarbonyl cycloalkyloxycarbonyl, and isopropyloxycarbonyl, are even less labile and require stronger acids, such as hydrogen fluoride, hydrogen bromide, or boron trifluoroacetate in trifluoroacetic acid, for their removal.

Example of amino acid protecting groups include:

(1) for an α-amino group, (a) aromatic urethane-type protecting groups, such as fluorenylmethyloxycarbonyl (FMOC); (b) aliphatic urethane-type protecting groups, such as BOC, t-amyloxycarbonyl, isopropyloxycarbonyl, 2-(p-biphenylyl)isopropyloxycarbonyl, allyloxycarbonyl and the like; (c) cycloalkyl urethane-type protecting groups, such as cyclopentyloxycarbonyl, adamantyloxycarbonyl, and cyclohexyloxycarbonyl; and (d) allyloxycarbonyl. The preferred α-amino protecting groups are BOC or FMOC.

(2) for the side chain amino group present in Lys, protecting groups—include any of the groups mentioned above in (1) such as BOC, p-chlorobenzyloxycarbonyl, etc.

(3) for the guanidino group of Arg, protecting groups preferably include nitro, or 2,2,5,7,8-pentamethylchroman-6-sulfonyl or 2,3,6-trimethyl-4-methoxyphenylsulfonyl.

(4) for the hydroxyl group of Ser, Thr, or Tyr, protecting include, for example, t-butyl; benzyl (BZL); substituted BZL groups, such as p-methoxybenzyl, p-nitrobenzyl, p-chlorobenzyl, o-chlorobenzyl, and 2,6-dichlorobenzyl.

(5) for the carboxyl group of Asp or Glu, protecting groups include, for example, by esterification using groups such as t-butyl, or preferably benzyl.

(6) for the imidazole nitrogen of His, suitable protecting groups include the benzyloxymethyl group (7) for the phenolic hydroxyl group of Tyr, protecting groups such as tetrahydropyranyl, tert-butyl, trityl, benzyl, chlorobenzyl, 4-bromobenzyl, and 2,6-dichlorobenzyl are suitably employed. The preferred protecting group is bromobenzyloxycarbonyl.

(8) for the side chain sulfhydryl group of cysteine, trityl is preferably employed as a protecting group.

Following the coupling of the BOC-protected amino acid to the support reagent, the α-amino protecting group is removed, such as by using trifluoroacetic acid (TFA) in methylene chloride or TFA alone. The deprotection is carried out at a temperature of from about 0° C. to about ambient temperature. Other suitable cleaving reagents, such as HCl in dioxane, and conditions for removal of specific α-amino protecting groups are described in Shroder & Lubke, supra, Chapter I, pages 72–75.

After the α-amino protecting group is removed, the remaining α-amino and side-chain protected amino acids are coupled stepwise in the desired order. As an alternative to adding each amino acid separately in the synthesis, some may be coupled to one another prior to their addition to the solid-base synthesizer so as to give a dipeptide or tripeptide analog. The selection of an appropriate coupling reagent is within the skill of the art. Particularly suitable as a coupling reagent is N,N'-dicyclohexyl carbodiimide or diisopropylcarbodiimide.

Each protected amino acid or amino acid sequence to be coupled to the growing peptide sequence or chain is introduced into the solid-phase reactor in excess, and the coupling is suitably carried out in a medium of suitable solvent such as dimethylformamide (DMF) or $CH_2Cl_2$ or mixtures thereof. If incomplete coupling occurs, the coupling procedure is repeated before removal of the α-amino protecting group of the product peptide sequence prior to the coupling of the next amino acid. The success of the coupling reaction at each stage of the synthesis may be monitored. A preferred method of monitoring the synthesis uses by the ninhydrin reaction, as described by Kaiser et al., *Anal. Bio-*

*chem* 34:595 (1970). The coupling reactions can be performed automatically using well known methods and instruments, for example, a Biosearch 9550 Peptide Synthesizer or Applied Biosystems Model 430A peptide synthesizer.

Upon completion of the desired peptide sequence, the protected peptide aldehyde is cleaved from the resin support, and protecting groups are removed. The cleavage reaction and removal of the protecting groups may be suitably accomplished simultaneously or stepwise. It will also be recognized that the protecting groups present on the N-terminal α-amino groups may be removed preferentially either before or after the protected peptide is cleaved from the support.

Purification of the polypeptide analogs prepared using the reagents of the present invention is typically achieved using conventional procedures such as preparative HPLC (including reversed phase HPLC) or other known chromatography, affinity chromatography (including monoclonal antibody columns) or countercurrent distribution.

B. General Preparation of Support Reagents (FIG. 2)

FIG. 2 depicts alternative generalized reaction schemes for the preparation of support reagents of the present invention. Blocking group, B1, denotes a protecting group which is removable under non-adverse conditions.

Figure 2A:
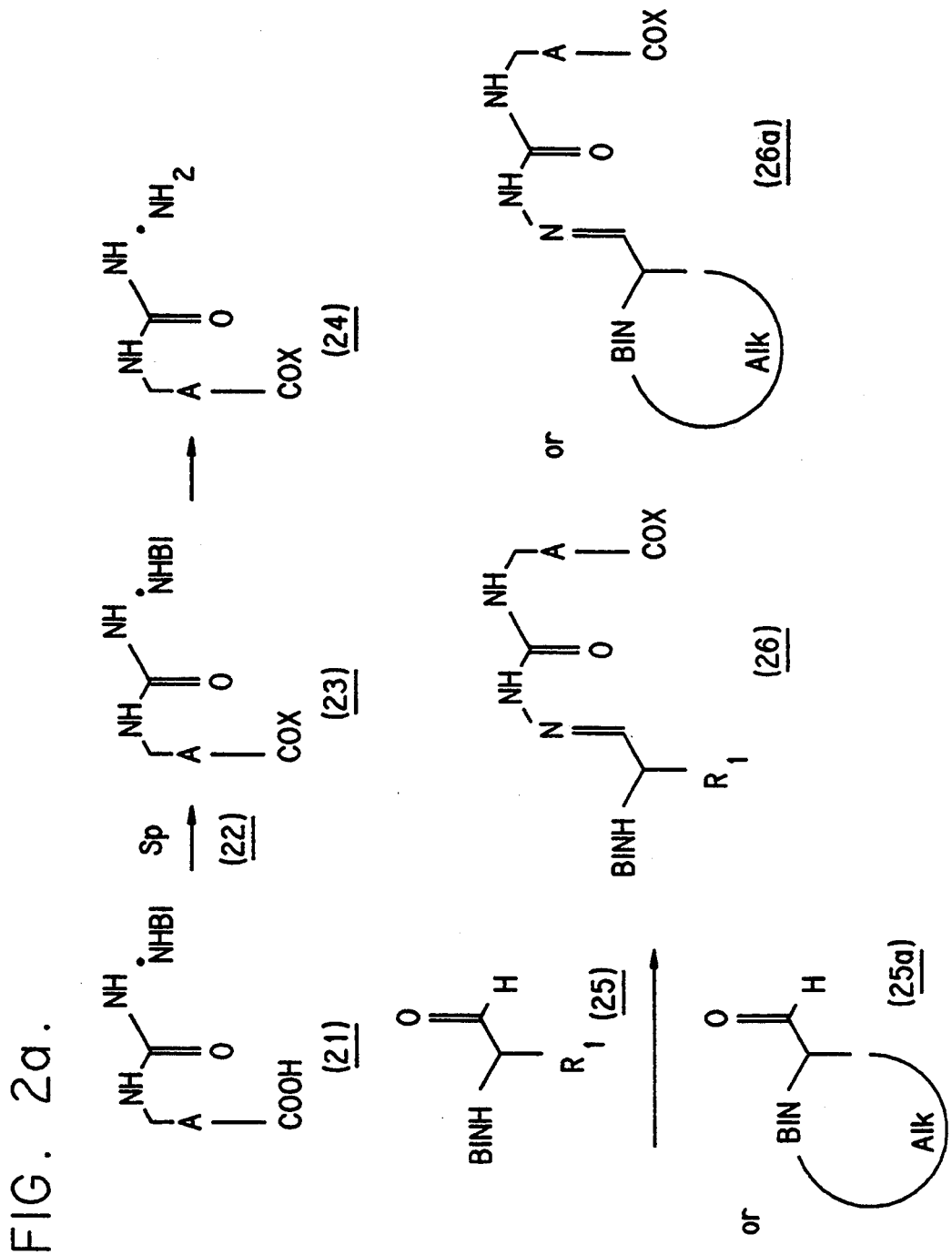
FIGS. 2A and 2B depict reaction schemes for the preparation of support reagents of the present invention.

According to FIG. 2A, protected semicarbazide moiety (21) is reacted with support (22) to give protected intermediate (23). The protecting group of intermediate (23) is removed under nonadverse conditions to give deprotected intermediate (24). Deprotected intermediate (24) is then reacted with α-aminoprotected amino acid aldehyde (25) or (25a) to give the appropriate support regent (26) or (26a) in a reaction which preserves the chirality of the amino acid aldehyde. Although FIG. 2A does not depict the stereochemical configuration of amino acid aldehyde (25), if either the L-isomer the D-isomer (as opposed to a racemic mixture) is employed, the stereochemistry of its chiral center will be conserved.

Figure 2B:
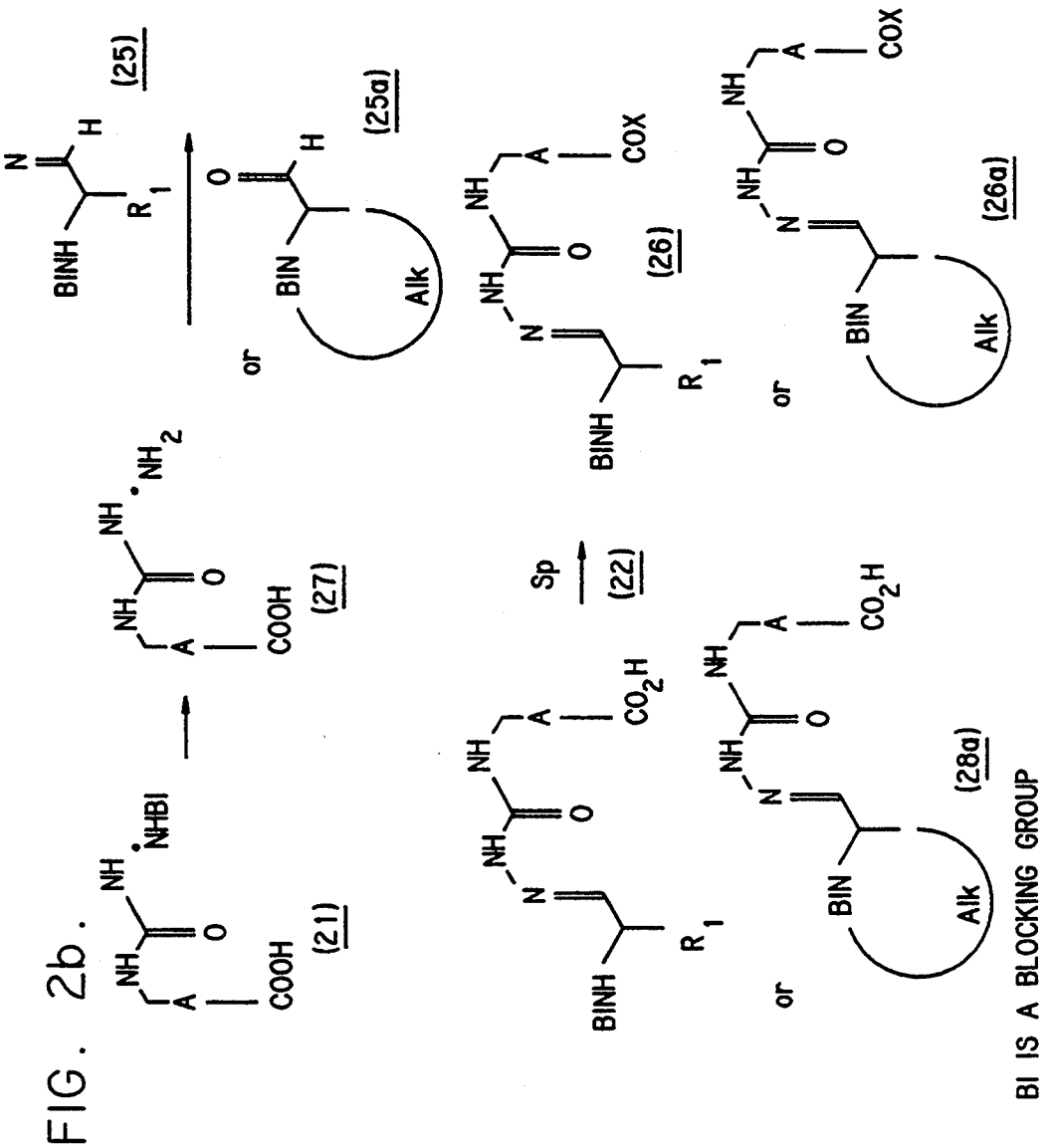

According to FIG. 2B, the protecting group, Pr, of protected semicarbazide moiety (21) is removed under non-adverse conditions. Deprotected semicarbazide moiety (27) is reacted with α-amino protected amino acid aldehyde (25) or (25a) to give semicarbazone intermediate (28) or (28a), as appropriate. The resulting intermediate is reacted with support (22) to give the appropriate support regent (26) or (26a) in a reaction which maintains the stereochemistry of the chiral center of amino acid aldehyde (25). Thus, if either the D- or the L- isomer of (25) (as opposed to a racemic mixture) is used, the stereochemistry of the chiral center will be conserved.

C. Preparation of α-Aminoprotected Amino Acid Aldehydes

Figure 3:
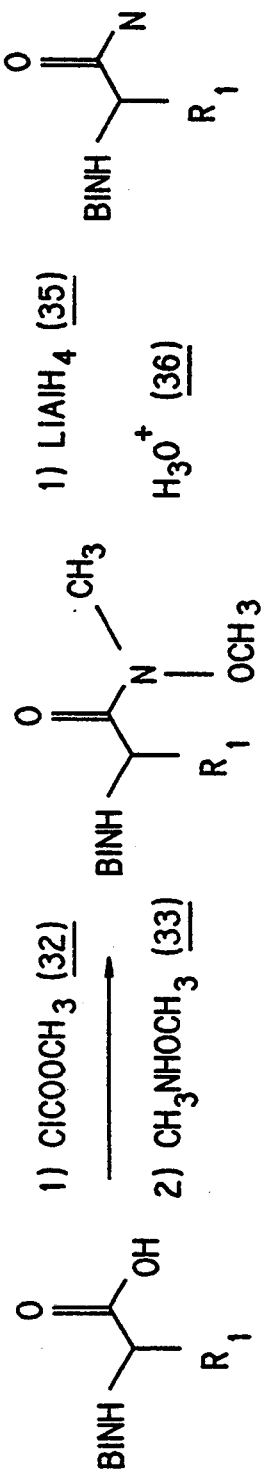
FIG. 3 depicts a reaction scheme for the preparation of $\alpha$-protected amino acid analogs which may be used in the preparation of the support reagents of the present invention.

The α-aminoprotected amino acid aldehydes (25) and (25a) of FIG. 2 may be prepared as described in Examples 1 to 18. FIG. 3 depicts one preferred reaction scheme for preparing aldehydes of formula (25) and (25a). In FIG. 3, blocking group, B1, denotes a protecting group which is removable under non-adverse conditions.

According to FIG. 3, a mixture of α-amino protected amino acid (31) or (31a), where B1 is a protecting group removable under nonadverse conditions, and methylchloroformate (32) in solvent is reacted with a mixture of dimethylhydroxylamine (33) to give the carboxamide (34) or (34c). The carboxamide (34) or (34a) is reacted with lithium aluminium hydride and then worked-up under acid conditions (36) to given the resulting α-amino protected amino acid aldehyde (25) or (25b).

DESCRIPTION OF PREFERRED EMBODIMENTS

Figure 1C:
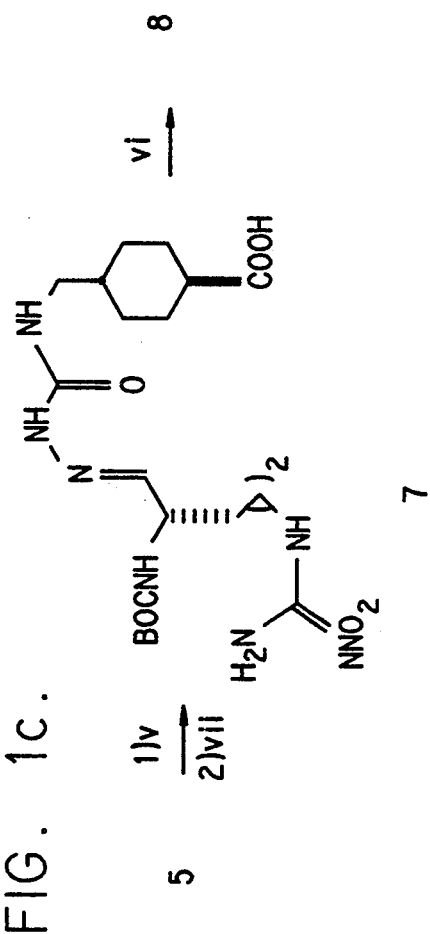
Figure 1B:
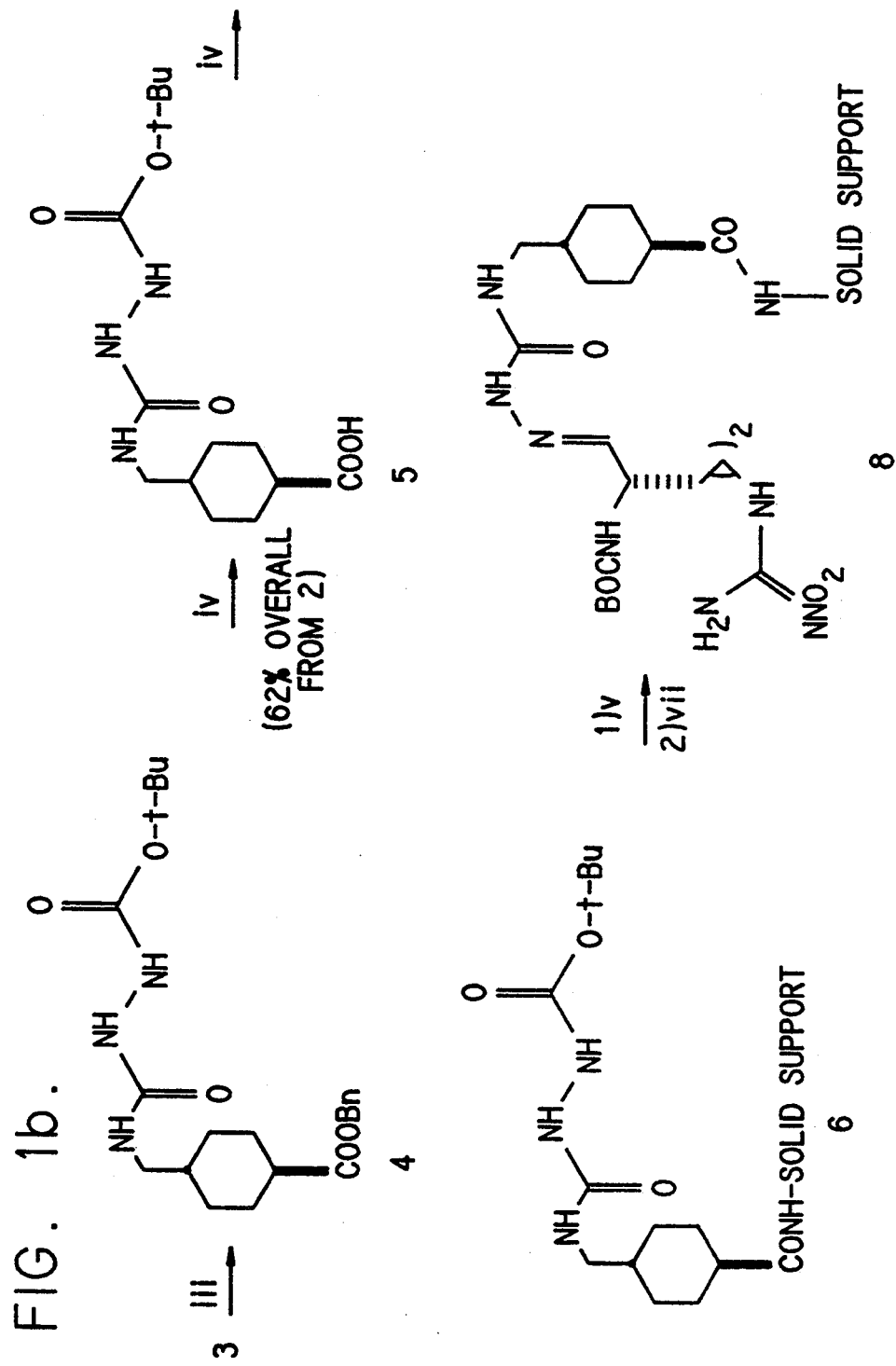

A. Preparation of Preferred Support Reagents Comprising Semicarbizide and Semicarbazone Linker Moieties FIG. 1 depicts a general reaction scheme for the synthesis of certain preferred semicarbazide and semicarbazone linker moieties and the support reagents incorporating those moieties. The reaction of t-butylcarbazate with carbonyldiimidazole gives an intermediate (having presumed structure 3) which is then allowed to react directly with epsilon amino ester (2). Epsilon amino ester (2) may be conveniently prepared from the commercially available trans-4-aminomethylcyclohexane carboxylic acid. The resulting protected semicarbazide (4) can be isolated by chromatography or alternatively may be converted directly to crystalline carboxylic acid (5), without further isolation in an approximately 62% overall yield. The free semicarbazide salt is prepared by allowing trifluoroacetic acid (TFA) to react with (5).

According to procedure A, carboxylic acid (5) is allowed to react with an insoluble amine resin such as methylbenzhydrylamine (MBHA). The reaction product is treated successively with TFA and then with the protected amino acid aldehyde α-t-butoxycarbonyl-N$^g$-nitroarginal (1) to give support (8). Alternatively, other suitably protected amino acid aldehydes may be substituted for (1).

Procedure B depicts an alternative protocol for the preparation of support regents of the present invention. According to Procedure B, preformed semicarbazone (7) is allowed to react directly with the resin (for example an amine resin such as MBHA). Procedure B may be preferred since support reagents having high substitution of semicarbazone linking moiety are readily obtained.

In the preparation of the preferred SAAA support reagents of the present invention by attachment to the novel linker moieties, polymeric resins having one or more of the following characteristics are particularly suitable:

(1) Resins which are insoluble in polar aprotic solvents such as dimethyl formamide (DMF), N-methylpyrrolidone, tetrahydrofuran (THF) and other solvents conventionally used in solid-phase peptide synthesis (such as dichloromethane or methanol).

(2) Resins which are microporous and which have high surface areas in polar aprotic solvents.

(3) Resins which are capable of being functionalized with groups which can react with a carboxylic acid group to form a bond which is stable during the subsequent addition of amino acids (or amino acid analogs) to the N-terminal end of the growing peptide chain.

(4) Resins which are stable in the presence of reagents such as TFA, diisopropylethyl amine, dicyclohexylcarbodiimide (DCC) and other reagents conventionally used in solid phase peptide synthesis.

Suitable resins having the above properties include commercially available resins which include P-methyl-(benzhydrylamine) (MBHA) or aminomethylated 1% divinylbenzene crosslinked polystyrene resins. Other suitable functionalized supports include pellicular and macroporous insoluble supports known to those skilled in the art (See, e.g., G. Barany and R. B. Merrifield, "Solid-Phase Peptide Synthesis," in *The Peptides*, Volume 2, pages (1–2984 (Academic Press, New York 1980)).

B. Preparation of Peptide Analogs Using Preferred Support Reagents

In the preparation of peptide aldehydes, SAAA resin (8) is added to the reaction vessel of an automated or semi-automated synthesizer. In the first synthesis, the t-butoxycarbonyl (BOC) protecting group on an α-amino group is removed with an acid such as TFA to give the resulting free amine. The amino group is coupled to a suitably activated carboxyl group of a blocked amino acid, using a suitable reagent such as DCC. The resulting resin undergoes a series of washing steps between each reaction. The addition cycle can then be repeated using the next α-blocked amino acid until the desired peptide sequence is complete. When the sequence is complete, the peptide aldehyde or analog may be released from the support (resin) by cleavage methods such as by treatment with aqueous formaldehyde and dilute acid to give the protected peptide aldehyde (or analog). If the product peptide analog has side chain or N-terminal protecting or blocking groups, these groups may be removed by conventional procedures such as by treatment with hydrogen and palladium catalysts (See Example 8). The peptide aldehydes may be further purified using procedures such as HPLC (See Examples 8 et seq.).

To assist in understanding the present invention, the following examples follow, which include the results of a series of experiments The following examples relating to this invention are illustrative an should not, of course, be construed as specifically limiting the invention. Moreover, such variations of the invention, now known or later developed, which would be within the purview of one skilled in the art are to be considered to fall within the scope of the present invention hereinafter claimed.

EXAMPLES

EXAMPLE 1

Preparation of α-N-t-butoxycarbonyl-N$^g$-nitroargininal

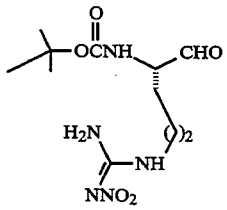

The following procedure for the synthesis of alpha-t-butoxycarbonyl-N$^g$-nitro-argininal is an example of a general procedure for the preparation of BOC-amino acid aldehydes, See Patel et al., Biochim. Biophys. Acta, 748, 321–330 (1983).

In 200 ML dry THF, 12.7 g BOC-N$^g$-nitro-arginine (40 mmoles) and 7.0 g carbonyldiimidazole (CDI, 43 mmoles) were added at room temperature and allowed to stir for 30 minutes The reaction mixture was cooled to $-78°$ C. and 35 mmoles of LiAlH$_4$ (1M in THF) were added dropwise over thirty minutes. The reaction mixture was allowed to stir for an additional hour at $-78°$ C. Next, 18 mL of acetone was added and the resulting mixture was quickly added to 400 mL of 1N HCl. The mixture was extracted twice with 100 mL of ethyl acetate. The ethyl acetate washes were combined and then washed two times each with 100 mL water, 100 mL saturated NaHCO$_3$ and 100 mL saturated NaCl (brine). The solution was dried (MgSO$_4$) and concentrated to a foam. The crude weight of the alpha-t-butoxycarbonyl-N$^g$-nitro-argininal was 6.36 g (21 mmole; yield 52%).

EXAMPLE 1A

Preparation of α-N-t-butoxycarbonyl-N$^g$-nitroargininal

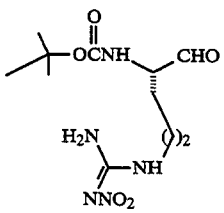

The following procedure for the synthesis of alpha-t-butoxycarbonyl-N$^g$-nitro-argininal (1) is a modification of the procedure of Fehrentz, J. A. and Castro, B., *Synthesis*, 676 (1983).

BOC-N$^g$-nitroarginine was obtained from Calbiochem. N-methylpiperidine, N,O-dimethylhydroxylamine hydrochloride and isobutylchloroformate, and lithium aluminum hydride were obtained from Aldrich chemical Company, Inc. Dichloromethane, ethyl acetate, methanol and tetrahydrofuran were obtained from Fisher Scientific Company.

11.4 mL of N-methylpiperidine was slowly added to a stirred suspension of 8.42 g (94 mmole) of N,O-dimethylhydroxylamine in 75 mL dichloromethane which had been cooled to about 0° C. The solution was allowed to stir for 20 minutes which gave the free hydroxylamine, then was kept cold for use in the next step.

In a separate flask, 30.0 g (94 mmole) of Boc-N$^g$-nitroarginine was dissolved by heating in about 1400 mL of tetrahydrofuran and cooled under nitrogen to 0° C. 11.4 mL of N-methylpiperidine and 12.14 mL (94 mmole) of isobutylchloroformate was added and the mixture stirred for 10 minutes. The free hydroxylamine prepared above was added all at once and the reaction mixture was allowed to warm to room temperature then stirred overnight.

The resulting precipitate was filtered off, then washed with 200 mL of tetrahydrofuran. After concentrating the filtrates to about 150 mL under vacuum, 200 mL of ethyl acetate was added, followed by ice to cool the solution. The cooled solution was washed with two 75 mL portions of 0.2N hydrochloric acid, two 75 mL portions of 0.5N sodium hydroxide, one portion of 75 mL of brine, then was dried over anhydrous magnesium sulfate. Upon concentration in vacuum, 22.7 g (70% yield) of solid BOC-N$^g$-nitroarginine N-methyl-O-methylcarboxamide was recovered. Thin layer chromatographic analysis in 9:1 dichloromethane/methanol (silica gel) showed one spot.

A flask was placed under a nitrogen atmosphere and cooled to $-50°$ C., then charged with 70 mL (70 mmole) of 1N lithium hydride (in tetrahydrofuran) and 500 mL of dry tetrahydrofuran. 50 mL of a solution containing 66 mmole of BOC-N$^g$-nitroarginine N-methyl-O-methylcarboxamide in dry tetrahydrofuran was slowly added while the temperature of the reaction mixture was maintained at −50° C. After allowing the reaction mixture to warm to 0° C. by removal of the cooling, it was recooled to −30° C., at which temperature, 100 mL (0.2 mole) of 2N potassium bisulfate was added with stirring over about a 10 to 15 minute period. The reaction mixture was then allowed to stir at room temperature for 2 hours. After filtering off the precipitate, the filtrate was concentrated to 100 mL under vacuum. The concentrate was combined with 200 mL ethyl acetate, then washed with two 50 mL portions of 1N hydrochloric acid, two 50 mL portions of saturated sodium bicarbonate, one 50 mL portion of brine, then was dried over anhydrous magnesium sulfate. The mixture was concentrated under vacuum to yield 13.6 g (70%) of the titled compound.

EXAMPLE 2

Preparation of Trans-4-(Amino methyl)-cyclohexane carboxylic acid benzyl ester para-toluenesulfonate salt (2)

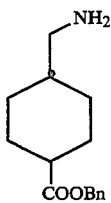

Trans-4-(aminomethyl)-cyclohexane carboxylic acid (50 g (0.318 moles)), p-toluenesulfonic acid (61.7 g (0.324 mmoles)), benzyl alcohol (250 mL; 2.4 moles) and toluene (250 mL) were combined and stirred. The resulting mixture was refluxed for 24 hours and the liberated water was removed azeotropically using a Dean-Stark apparatus. A clear solution was obtained after 5 hours of refluxing. The solution was allowed to cool to room temperature and the product crystallized. The mixture was vacuum filtered, washed with ether and dried in a vacuum oven to give 128.12 g (96% yield) of the above-identified product. $^1$H NMR (CD$_3$OD) δ1.05 (, 2H), 1.43 (m, 2H), 1.59 (m, 1H), 1.85 (m, 2H), 2.03 (m, 2H), 2.33 (m, 1H), 2.35 (s, 3H), 2.75 (d, 2H, 5.09 (s, 2H), 7.23 (d, 2H), 7.32 (m, 5H), 7.69 (d, 2H). M.P. 154°–156° C.

Reference: Greenstein, Jesse P.; Winitz, Milton, *Chemistry of the Amino Acids.*, vol. 2, p. 942, (1986).

EXAMPLE 3

Preparation of 1-t-Butoxycarbonylsemicarbozidyl-trans-4-methyl cyclohexane carboxylic acid benzyl ester (4)

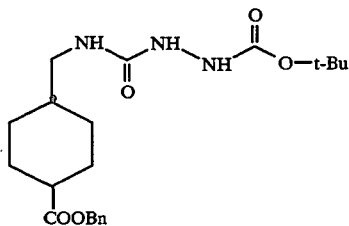

Carbonyldiimidazole (CDI) (3.24 g (0.02 moles) was dissolved in 45 mL of dimethylformamide (DMF) at room temperature under nitrogen. To that mixture, a solution of 2.48 g (0.02 moles ) t-butyl carbazate in 45 mL DMF was added dropwise. Next 8.38 g (0.02 moles ) of solid benzyl ester 2 (the product of Example 2) was added, followed by the dropwise addition of 3.06 mL of triethylamine (TEA) over a 30 minute period. The reaction mixture was allowed to stir at room temperature under nitrogen for one hour. Water (100 mL) was added to the mixture and this mixture was extracted three times with 50 mL of ethyl acetate. The ethyl acetate layers were combined and extracted two times each with 75 mL 1N HCl, H$_2$O, 5% NaHCO$_3$, and saturated NaCl, and then dried with MgSO$_4$. The mixture was filtered and the solution was concentrated to give an oil. This oil crystallized on standing. This material may be purified further by recrystallization, but may be used directly in the next procedure described in Example 4 without additional purification and/or isolation. M.P.=106°–108° C. (EtOAc/hexane) $^1$H NMR (CDCl$_3$) δ0.94 (m, 2H), 1.42 (m, 2H), 1.45 (s, 9H), 1.81 (m, 2H), 2.02 (m, 2H), 2.27 (m, 1H), 3.17 (t, 2H), 5.09 (s, 2H), 5.51 (t, 1H), 6.46 (s, 2H), 7.34 (m, 4H).

EXAMPLE 4

Preparation of 1-(t-Butoxycarbonyl)-semicarbazidyl-trans-4-methyl-cyclohexane carboxylic acid (5)

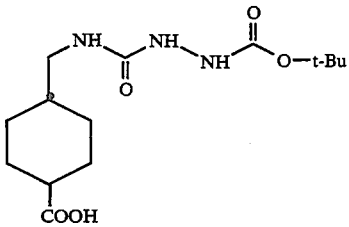

To the crude BOC-benzyl ester 4 (product of Example 3), 250 mL of methanol (MeOH) and 500 mg of 10% palladium on activated carbon were added. After shaking on the hydrogenator for one hour at 5 psi, the mixture was filtered with Celite through a fine fritted filter. The solution was concentrated to a foam, methylene chloride was added and a precipitate formed. The mixture was kept 5° C. for 565 hours. The crystallized material was filtered with ether and 4.0 g of crude product was obtained (12.7 mmoles; yield: 62% overall yield from compound 2.) $^1$H NMR (CD$_3$OD), δ0.96, (m, 2H), 1.42 (m, 2H), 1.46 (s, 9H), 1.82 (m, 2H), 1.97 (m, 2H), 2.18 (m, 1H), 3.0 (t, 2H). M.P.=185°–189° C.

EXAMPLE 5

Preparation of Semicarbazidyl-trans-4-methyl cyclohexane carboxylic acid trifluoroacetate salt

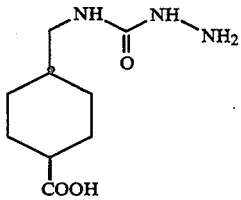

Compound 5 (the product of Example 4), (315 mg (1 mmole)) was added to 10 mL of trifluoroacetic acid (TFA) at 0° C. and the resulting solution was allowed to stir for 30 minutes. After this time the solution was added dropwise to 75 mL of etcher. A precipitate formed. The mixture was filtered and washed with ether. Weight of crude product was 254 mg (0.77 mmoles; yield (77%)). $^1$H NMR (CD$_3$OD), δ1.0 (m, 2H), 1.38 (m, 2H), 1.43 (m, 1H), 1.84 (m, 2H), 2.01 (m, 2H), 2.22 (m, 1H), 2.04 (d, 2H). M.P. =154°–156° C.

EXAMPLE 6

Preparation of alpha-N-(t-Butoxycarbonyl)-N$^g$-nitro-argininal-semicarbazonyl-trans-4-methyl-cyclohexane carboxylic acid (7)

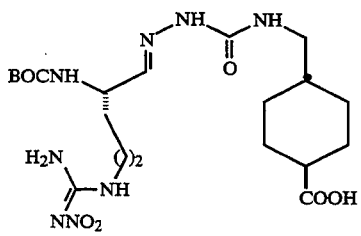

A solution of 13.7 g (41.6 mmoles) of the product of Example 5, 18.0 g (~59 mmoles) of crude 1 (the product of Example 1) in 135 mL ethanol containing 45 mL of water, was treated with 9.41 g (69 mmoles) of NaOAc and refluxed for one hour. This solution was allowed to cool and then poured into 0.1N HCl and extracted three times with ethyl acetate. The combined organic phase was washed with water, then brine, dried (over MgSO$_4$) and concentrated to a small volume. This cloudy mixture was allowed to set overnight at 5° C. to precipitate the product, which was isolated by filtration and dried under vacuum. This gave 9.9 g., 47% yield based on 6. $^1$H NMR (CD$_3$OD) δ1.0 (m, 2H), 1.43 (s, 9H), 1.45–2.20 (m, 13H), 3.09 (d, 2H), 3,30 (m, 2H), 4.18 (bs, 1H), 7.10 (d, 1H). M.P.=162°–163° C.

EXAMPLE 7

Synthesis of Semicarbazine Solid Support

A. Procedure A:

Coupling of Amino Acid Aldehydes to Modified Resin (1) Place 0.8 g (0.5 mmoles, 0.62 g/ml) of Methyl-benzhydrylamine (MBHA) resin in a reaction vessel. Note: All washes require 10 mL of solvent with agitation for 1.2 minutes. (2) Wash 1 time with dichloromethane (DCM). (3) Wash 3 times with dimethylformamide (DMF). (4) Wash 2 times with 10% diisopropylethylamine (DIEA)/DMF (5) Wash 4 times with DMF. (6) Add: 5 mL DMF
  1 mmole 4-Methylmorpholine (NMM)=102 µl
  1 mmole Benzotriazol-1-yloxy-tris-(dimethylamino) phosphonium-hexafluorophosphate (BOP reagent)=443 mg.
  1 mmole compound 5 (FIG. 1) from Example 4=315 mg (7) Mix on rotating wheel for 1 hour.
(8) Wash 3 times with DMF.
(9) Remove aliquot for ninhydrin test. Quantitate % coupling.
(10) Wash 3 times with DCM.
(11) Add 50% trifluoroacetic acid (TFA)/DCM and stir for 20 min.
(12) Wash 3 times with DCM. (Resin 6).
(13) Wash 2 times with 10% DIEA/DMF.
(14) In 5 mL DMF add 6 mmole=1.82 g BOC-nitro-argininal.
(15) Quantitatively transfer mixture to a test tube.
(16) Heat to 40° C. in an oil bath while bubbling in nitrogen gas for stirring.
(17) Let reaction proceed for 30 hours.
(18) Remove aliquot and wash 2 times with DCM. Note: Steps 19–23 pertain to the aliquot.
(19) Add 10 mL 50% TFA/DCM and stir for 20 min.
(20) Wash 3 times with DMF.
(21) Wash 2 times with 10% DIEA/DMF.
(22) Wash 3 times with DMF.
(23) Ninhydrin as for step 9: quantitate % coupling.
(24) Acetylate the remaining resin.
  Wash 3 times with DMF
  Add 15 mL DMF
    0.47 mL acetic anhydride
    0.7 mL triethylamine (TEA)
  Stir for 30 minutes
  Wash 3 times each with: DMF, DCM, MeOH and either.
(25) Let dry and weigh.

Synthesis of Semicarbazone Solid Support

B. Procedure B
(1) Place 0.8 g (0.5 mmoles, 0,62 g/mol) of Methyl-benzhydrylamine (MBHA) resin in a reaction vessel. Note: all washes require 10 mL of solvent with agitation for 1–2 minutes.
(2) Wash 1 time with dichloromethane (DCM).
(3) Wash 3 times with dimethylformamide (DMF).
(4) Wash 2 times with 10% diisopropylethylamine (DIEA)/DMF
(5) Wash 4 times with DMF.
(6) Add: 5 mL DMF
  1 mmole 4-Methylmorpholine(nmm)=102 µl
  1 mmole Benzotriazol-1-yloxy-tris-(dimethylamino) phosphonium-hexafluorophosphate (BOP reagent)=443 mg.
  1 mmole alpha-(4-butoxycarbonyl)-N$^g$-niroargininal-semicarbazonyl-trans-4-methyl-cyclohexane carboxylic acid 7=500 mg
(7) Mix on rotating wheel on 16 hours.
(8) Wash 3 times with DMF.
(9) Wash 2 times with 10% DIEA/DMF.
(10) Wash three times with DMF.
(11) Wash successively with DCM, MeOH and ether.
(12) Let dry and weigh.

The resulting resin 8 obtained by Procedure B showed 98–99% coupling yield by ninhydrin.

Both procedures A and B will give the resin 8 shown in FIG. 1. This resin can then be extended at the N-terminus with amino acids or amino acid analogs on a conventional peptide synthesizer using standard t-BOC methodology. The resulting protected peptide analog can be cleaved from support with formaldehyde, and deprotected with hydrogen/Pd, if desired. The nitro group can be removed from the guanidine group without reduction of the aldehyde.

EXAMPLES OF AUTOMATED SYNTHESIS OF PEPTIDE ALDEHYDES

The automated synthesis of peptide aldehydes was performed on an Applied Biosystems model 430A peptide synthesizer using the BOC chemistry conditions in the 430A users manual. The following examples are representative only. It will be apparent to those skilled in the art that the use of other alpha-amino protecting groups, different cleavage or work-up conditions, or purification schemes, may also be utilized. It will also be recognized that the synthesis of other peptide aldehydes will often require the use of other side-chain protecting groups, or combination of protecting groups, that are also compatible with the instant process. It will also be noted that due to the reactive nature of the aldehyde group it may not be possible to synthesize and isolate all possible sequences of peptide aldehydes.

EXAMPLE 8

Synthesis of alpha-t-Butoxycarbonyl-D-Leu-L-Pro-L-Argininal

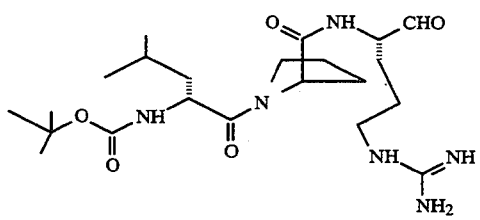

The above-identified compound was prepared using 500 mg SAAA support 8, α-BOC amino acids and standard solid phase peptide synthesis as described above. The BOC protecting groups were removed using a solution of 50% TFA/DCM. The resin (support) was neutralized with 10% diisopropylethylamine in DCM. Coupling of amino acids to support reagent (and growing amino-acid-support chain) was performed in DMF with DCC and 1-hydroxybenztriazole. To 470 mg of the resulting peptide analog resin, 5 mL tetrahydrofuran (THF), 1 mL acetic acid, 1 mL formaldehyde and 100 μl 1N HCl are combined and stirred for about one hour. The solution is filtered and washed with 10 mL THF. The filtrate is diluted with 100 mL water and extracted with ethyl acetate. The ethyl acetate phase is washed with brine, dried (magnesium sulfate), and concentrated. The nitro protecting group and other hydrogen-removable protecting groups are removed by hydrogenation in 10 mL 10% water/methanol with 300 μl 1N HCl and 200 mg palladium on carbon at 5 psi for 45 minutes. The mixture is filtered through a fine fritted filter with Celite, washed with methanol/water and concentrated to give the crude peptide aldehyde.

The resulting peptide aldehyde can then be further isolated by C-18 reverse phase HPLC, using an aqueous/acetonitrile (0.01% TFA) system to give the corresponding TFA salts. The product is then purified using reverse phase high performance chromatography on a 10 micron 300 angstrom pore size C-18 packing. The column was eluted with an aqueous gradient of 0.1% trifluoroacetic and acetonitrile, gradient going from 5% to 40% acetonitrile containing 0.01% trifluoroacetic acid. Lyophilization of the appropriate fractions gave the above-identified peptide aldehyde as the trifluoroacetate salt. FAB mass spectrum:calculated MW=468, observed MW=468.

EXAMPLE 9

Synthesis of alpha-t-Butoxycarbonyl-D-Phe-L-Pro-L-Argininal

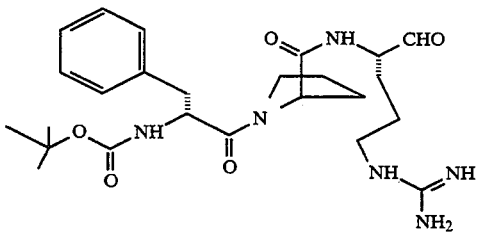

The above-identified compound was prepared using SAAA support 8, α-BOC amino acids and standard solid phase peptide synthesis as described in Example 8. The resin was cleaved, and deprotected, as described in Example 8. The crude product was purified using reverse phase high performance chromatography as described in Example 8. FAB mass spectrum: calc. mw=502; obs. mw=502.

EXAMPLE 10

Synthesis of alpha-t-Butoxycarbonyl-L-Leu-L-Pro-L-Argininal

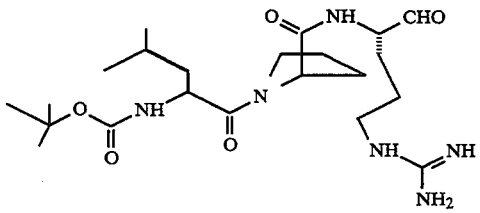

The above-identified compound was prepared using SAAA support 8, α-BOC amino acids and standard solid phase peptide synthesis as described in Example 8. The resin was cleaved, and deprotected, as described in Example 8. The crude product was purified using reverse phase high performance chromatography as described in Example 8. FAB mass spectrum: calc. mw=468; obs. mw=468.

EXAMPLE 11

Synthesis of alpha-t-Butoxycarbonyl-L-Leu-L-Tyr-L-Argininal

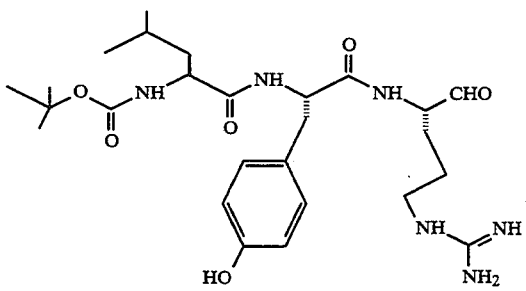

The above-identified compound was prepared using SAAA support 8, α-BOC amino acids, 2-bromobenzyloxy-carbonyl protected tyrosine, and standard solid phase peptide synthesis as described in Example 8. The resin was cleaved, and deprotected, as described in Example 8. The crude product was purified using reverse phase high performance chromatography as described in Example 8. FAB mass spectrum: calc. mw=534; obs. mw=534.

EXAMPLE 12

Synthesis of alpha-t-Butoxycarbonyl-L-Leu-L-Phe-L-Argininal

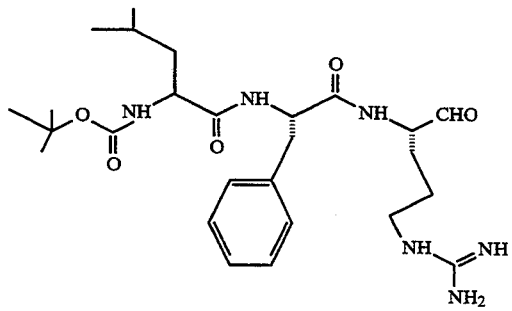

The above-identified compound was prepared using SAAA support 8, α-BOC amino acids and standard solid phase peptide synthesis as described in Example 8. The resin was cleaved, and deprotected, as described in Example 8. The crude product was purified using reverse phase high performance chromatography as described in Example 8. FAB mass spectrum: calc. mw=518; obs. mw=518.

EXAMPLE 13

Synthesis of alpha-t-Butoxycarbonyl-L-Asp-L-Pro-L-Argininal.

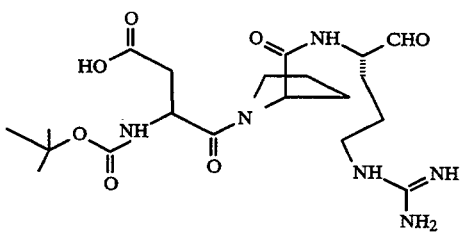

The above-identified compound was prepared using SAAA support 8, using α-BOC amino acids, benzyl ester protection of aspartic acid and standard solid phase peptide synthesis as described in Example 8. The resin was cleaved, and deprotected, as described in Example 8. The crude product was purified using reverse phase high performance chromatography as described in Example 8. FAB mass spectrum: calc. mw=470; obs. mw=470.

EXAMPLE 14

Synthesis of alpha-t-Butoxycarbonyl-D-Leu-L-Ser-L-Argininal

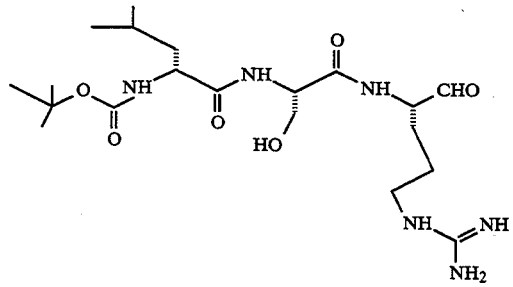

The above-identified compound was prepared using SAAA support 8, using α-BOC amino acids, O-benzyl protection for serine, and standard solid phase peptide synthesis as described above. The resin was cleaved, and deprotected, as described below. The crude product was purified using reverse phase high performance chromatography as described in Example 8. FAB mass spectrum: calc. mw=458; obs. mw=458.

EXAMPLE 15

Synthesis of alpha-t-Butoxycarbonyl-L-Phe-L-Trp-L-Argininal

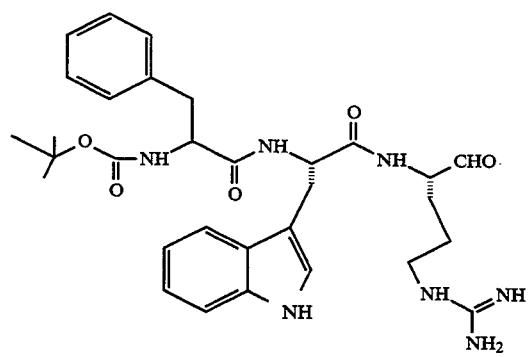

The above identified compound was prepared using SAAA support 8, using α-BOC amino acids, N-formyl-indole-Trp and standard solid phase peptide synthesis as described in Example 8. The resin was treated with piperidine using standard conditions, cleaved, and deprotected, as described in Example 8. The crude product was purified using reverse phase high performance chromatography as described in Example 8. FAB mass spectrum: calc. mw=591; obs. mw=591.

EXAMPLE 16

Synthesis of alpha-t-Butoxycarbonyl-L-Leu-D-Pro-L-Argininal

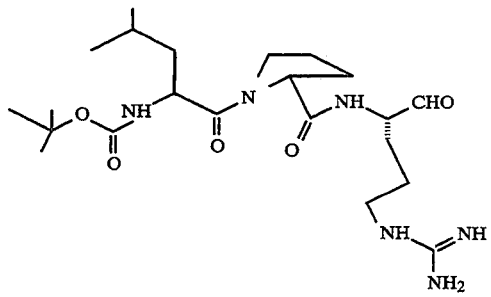

The title compound was prepared using SAAA support 8, α-Boc amino acids and standard solid phase peptide synthesis as described in Example 8. The resin was cleaved, and deprotected, as described in Example 8. The crude product was purified using reverse phase high performance chromatography as described for Example 8. FAB mass spectrum: calc. mw=468; obs. mw=468.

EXAMPLE 17

Cleavage of Peptide Aldehyde from Resin 470 mg of peptide aldehyde coupled to support (as prepared according to Examples 8–16), 5 ml THF, 1 mL acetic acid, 1 mL aqueous formaldehyde, and 100 ul 1N HCl are combined and stirred for 1 hour. The solution is filtered and washed with 10 mL THF and the filtrate is diluted with 100 mL of water and extracted with ethyl acetate. The ethyl acetate phase is washed with brine, dried (MgSO$_4$) and concentrated. The nitro group and other hydrogen removable protecting groups are removed, when it is desirable, by hydrogenation in 10 mL 10% H$_2$O/MeOH with 300 μl 1N HCl and 200 mg activated palladium on carbon at 5 psi for 45 minutes. The mixture is filtered through a fine fritted filter with Celite, washed with MeOH/water and concentrated to give the crude peptide. The resulting peptide aldehyde can then be purified by C-18 reverse phase HPLC, using an aqueous/acetonitrile (0.01% TFA) system to give the corresponding TFA salts.

EXAMPLE 18

Preparation of α-N-t-butoxycarbonyl-L-leucinal

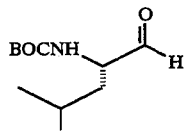

A. Preparation of α-t-butoxycarbonyl-L-leucine-N-methyl-O-methylcarboxamide.

A 1-L, three-necked, round-bottom flask is equipped with a mechanical stirrer, an electronic digital thermometer, and a graduated additional funnel. The flask is charged with 39.1 g (0.4 moles) of N,O-dimethylhydroxylamine hydrochloride (Aldrich Chemical Co.) and 236 mL methylene chloride. The suspension is stirred and cooled to 2° C. with an ice-water bath. N-methylpiperidine (Aldrich Chemical Co.), 48.8 mL (0.41 moles), is placed in the addition funnel and added dropwise while the temperature is maintained at about 2° C. (±2°). A clear, colorless solution results which is kept cold and is used in the following reaction.

A 5-L, three-necked, round-bottomed flask is equipped with a mechanical stirrer, thermometer, and an addition funnel with drying tube, the flask is charged with 100 g (0.4 moles) of α-t-butoxylcarbonyl-L-leucine hydrate (Bachem, Inc.), 458 mL tetrahydrofuran (Fisher Scientific Co.) and 1.8 L methylene chloride. A clear solution results on stirring, which is cooled to −20° C. (±2°) by immersing the flask in a dry ice-2-propanol bath. N-methyl-piperidine, 48.8 mL (0.41 moles), is placed in the addition funnel and is added rapidly to the mixture, while the temperature is allowed to rise to about −12° C. (±2°). Methyl chloroformate (Aldrich Chemical Co.), 31 mL (0.4 moles) is then placed in the addition funnel and added rapidly to the mixture with good stirring, while the temperature is maintained at about −12° C. (±2°). Two minutes later the above-described solution of N,O-dimethylhydroxylamine is added. The cooling bath is removed and the clear solution is allowed to warm to room temperature over about 4 hours (and may be stirred overnight for convenience). The solution is then cooled to about 5° C. and extracted with two 500 mL portions of aqueous 0.2N hydrochloric acid and two 500 mL portions of aqueous 0.5N sodium hydroxide, while maintaining the organic phase at about 5° C. to about 15° C. during the extractions. The solution is washed with 500 mL of saturated aqueous sodium chloride solution, dried over magnesium sulfate and concentrated on a rotary evaporator at a bath temperature of about 30°–35° C. The residue is further evacuated on a Varian 5500 instrument (using a 250 mm×4.6 mm I.D. Alltech C-18 column with 60:40 methanol:0.5M NH$_4$H$_2$PO$_4$ as the mobile phase, UV detection at 210 nm).

B. Preparation of α-N-tert-butoxycarbonyl-L-leucinal

A 5-L, four-necked, round-bottomed flask is equipped with a mechanical stirrer, a thermometer, a pressure-equalizing addition funnel, and an air-cooled condenser fitted with an argon blanket adapter. The flask is charged under an argon blanket with 17.7 g (95% pure, 0.44 moles) lithium aluminum hydride (Alfa Products, Morton/Thiokol Inc.) and 1.5 L anhydrous ethyl ether (Fisher Scientific Co.). The resulting suspension is stirred at room temperature for about one hour or until most of the solid is finely dispersed. The flask is immersed in a dry ice-2-propanol bath and the suspension is cooled to about −45° C. A solution of the α-t-butoxycarbonyl-L-leucine N-methyl-O-methylcarboxamide (prepared according to paragraph A above), in 300 mL anhydrous ethyl ether is placed in the addition funnel and added to the lithium aluminum hydride suspension (which is cooled to about −45° C. before the addition) in a steady stream while maintaining the reaction temperature at about −35° C. (±3°). After the addition is complete, the cooling bath is removed and the mixture is stirred and is allowed to warm to about ±5°. Then, the mixture is once again cooled to about −35° C. and a solution of 96.4 g (0.171 moles) of sodium bisulfate (Matheson, Coleman and Bell, a saturated aqueous solution is obtained after stirring overnight) in 265 mL deionized water is placed in the addition funnel. The sodium bisulfate solution is added cautiously at first and then rapidly, while the temperature is allowed to rise to about −2° C. (±3°). The cooling bath is removed and the mixture is stirred for about one hour.

The reaction mixture is filtered through a 2 inch pad of celite. The filter cake is washed with two 500 mL portions of ethyl ether. The combined ether layers are washed in sequence with three 350 mL portions of cold (about 5° C.) 1N hydrochloric acid, two 350 mL portions of saturated aqueous sodium bicarbonate solution, and 350 mL saturated sodium chloride solution. The organic solution is dried over magnesium sulfate and evaporated on a rotary evaporator (bath at 30° C.), to give a residual, slightly cloudy syrup. The product is stored in a freezer (about −17° C.) prior to use, since it may racemize if stored at room temperature.

Reference:

Smart, B. E. (ed.), *Org. Syn.*, Volume 67, pages 69–75 (1988).

EXAMPLE 19

Preparation alpha-N-(t-Butoxycarbonyl)-leucinal-semicarbazonyl-trans-4-methyl-cyclohexane carboxylic acid

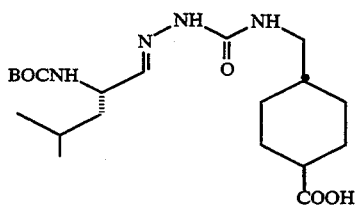

A solution of 13.7 g (41.6 mmoles) of the product of Example 5 and 8.81 g (45 mmoles) of alpha-N-t-butoxycarbonyl-leucinal in 135 mL ethanol containing 45 mL of water, is treated with 9.41 g (69 mmoles) of sodium acetate and refluxed for one hour. This solution is allowed to cool and then is poured into 0.1N HCl and is extracted three times with ethyl acetate. The combined organic phase is washed with water, then brine, dried (MgSO$_4$) and concentrated to a small volume. The product is purified by crystallization or column chromatography on silica gel.

EXAMPLE 20

Preparation of Leucinal Semicarbazone Solid Support

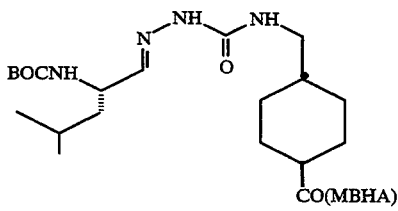

The procedure of Example 7B is followed except that an equamolar amount of α-N-(t-butoxycarbonyl)-leucinal-semicarbazonyl-trans-4-methyl-cyclohexane-carboxylic acid (the product of Example 19) is used in place of the product of Example 5. This procedure gives a solid support suitable for the synthesis of peptide C-terminal leucinals.

EXAMPLE 21

Preparation of alpha-N-(t-Butoxycarbonyl)-alaninal-semicarbazonyl-trans-4-methyl-cyclohexane Carboxylic Acid

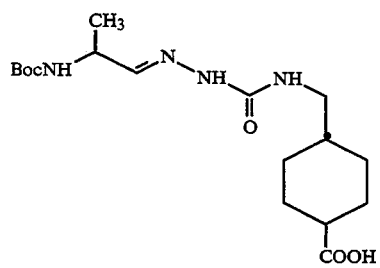

A solution of 1.04 g (6.0 mmoles) of the product of Example 5 and 2.90 g (8.8 mmoles) of alpha-t-butoxycarbonyl-alaninal in 36 mL of 15% aqueous ethanol, was treated with 1.63 g (12.0 mmoles) of sodium acetate trihydrate and the resulting solution was refluxed for one hour. This solution was allowed to cool and then poured into 0.1N HCl and extracted three times with ethyl acetate. The combined organic phase was washed with water, then brine, dried (MgSO$_4$) and concentrated to a small volume. The product was purified by crystallization from ethyl acetate/hexanes. This gave 1.43 g (64% yield) of a white solid: mp=194°–196° C. $^1$H NMR (CDCl$_3$) δ1.01 (m, 2H), 1.31 (d, J=5 Hz, 3H), 1.46 (s, 9H), 1.8–2.3 (m, 5H), 3.16 (bs, 2H), 4.38 (bs, 1H), 7.06 (d, J=3.5 Hz, 1H). Analysis; Calculated for C$_{17}$H$_{34}$N$_4$O$_5$: C, 55.1; H, 8.2; N, 15.1. Found: C, 53.7; H, 7.8; N, 14.0.

EXAMPLE 22

Preparation of Alaninal Semicarbazone Solid Support

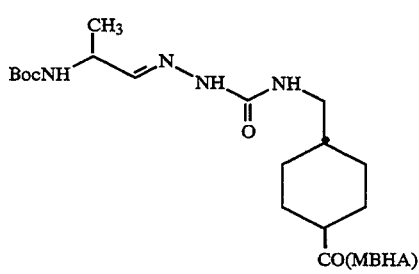

In preparing the above-identified product, the procedure described in Example 7B is followed except that an equimolar amount of the product of Example 21 is used in place of compound 7 (the product of Example 6). This procedure gives a solid support product suitable for the synthesis of peptide C-terminal alaninals, in 98–99.5% coupling yield (by ninhydrin).

EXAMPLE 23

Preparation of alpha-N-(t-Butoxycarbonyl)-valinal-semicarbazonyl-trans-4-methyl-cyclohexane Carboxylic Acid

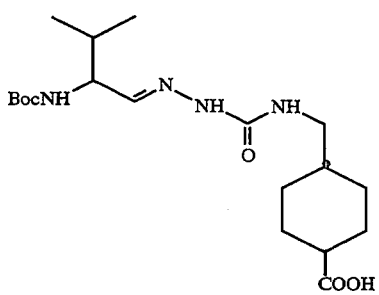

A solution of 2.3 g (10.5 mmoles) of the product of Example 5 and 5.5 g (16.7 mmoles) of alpha-N-t-butoxycarbonyl-valinal in 68 mL of 15% aqueous ethanol, was treated with 3.08 g (22.6 mmoles) of sodium acetate trihydrate and the resulting solution was refluxed for one hour. This solution was allowed to cool and then poured into 0.1N HCl and extracted three times with ethyl acetate. The combined organic phase was washed with water, then brine, dried (MgSO4) and concentrated to a small volume. The product was purified by crystallization from ethyl acetate/hexanes. This gave 3.83 g (91% yield) of a white solid: mp=144°-145° C. $^1$H NMR (CD$_3$OD) δ0.95 (d, J=7 Hz, 6H), 1.01 (m, 2H), 1.46 (s, 9H), 1.8-2.30 (m, 5H), 3.10 (bs, 2H), 3.98 (bs, 1H), 7.12 (d, J=3.5 Hz, 1H). Analysis; Calculated for C$_{19}$H$_{34}$N$_4$O$_5$: C, 57.3; H, 8.6; N, 14.1. Found: C, 56.3; H, 8.3; N, 13.7.

EXAMPLE 24

Preparation of Valinal Semicarbazone Solid Support

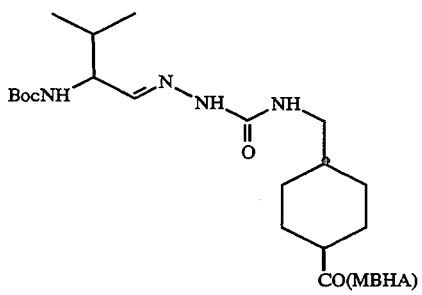

In preparing the above-identified product, the procedure described in Example 7B is followed except that an equimolar amount of the product of Example 23 is used in place of compound 7 (the product of Example 6). This procedure gives a solid support product suitable for the synthesis of peptide C-terminal valinals, in 98–99.5% coupling yield (by ninhydrin).

EXAMPLE 25

Preparation of alpha-N-(t-Butoxycarbonyl)-phenylalaninal-semicarbazonyl-trans-4-methyl-cyclohexane Carboxylic Acid

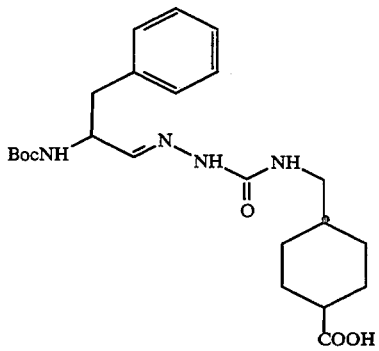

A solution of 2.5 g (10.0 mmoles) of the product of Example 5 and 3.6 g (11.0 mmoles) of alpha-N-t-butoxycarbonyl-phenylalaninal in 60 mL of 15% aqueous ethanol, was treated with 2.72 g (20.0 mmoles) of sodium acetate trihydrate and the resulting solution was refluxed for one hour. This solution was allowed to cool and then poured into 0.1N HCl and extracted three times with ethyl acetate. The combined organic phase was washed with water, then brine, dried (MgSO4) and concentrated to a small volume. The product was purified by crystallization from ethyl acetate/hexanes. This gave 3.4 g (78% yield) of a white solid: mp=173°-174° C. $^1$H NMR (CD$_3$OD) δ1.05 (m, 2H), 1.41 (s, 9H), 1.8-2.30 (m, 5H), 2.9-3.1 (m, 4H), 4.43 (bs, 1H), 7.1-7.3 (d, 6H). Analysis; Calculated for C$_{23}$H$_{34}$N$_4$O$_5$: C, 61.9; H, 7.7; N, 12.5. Found: C, 61.6; H, 7.7; N, 12.2.

EXAMPLE 26

Preparation of Phenylalaninal Semicarbazone Solid Support

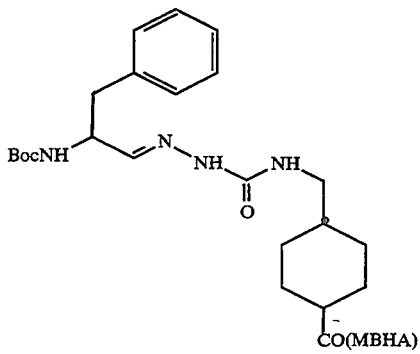

In preparing the above-identified product, the procedure described in Example 7B is followed except that an equimolar amount of the product of Example 25 is used in place of compound 7 (the product of Example 6). This procedure gives a solid support product suitable for the synthesis of peptide C-terminal phenylalaninals in 98–99.5% coupling yield (by ninhydrin).

EXAMPLE 27

Preparation of alpha-t-Butoxycarbonyl-L-Asp-(O-benzyl ester)-L-Pro-L-Valinal

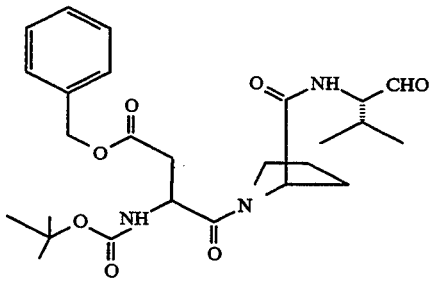

The title compound was prepared using 500 mg valinal SAAA support (product of Example 24), α-BOC-L-proline, α-BOC-O-benzyl aspartic acid and standard solid phase peptide synthesis as described above. A solution of 50% TFA/DCM was used to remove the BOC groups. The resin was neutralized with 10% diisopropylethylamine in DCM. Coupling was performed in DMF with DCC and 1-hydroxybenztriazole. To 470 mg of resulting peptide aldehyde resin (from above), 5 mL THF, 1 mL acetic acid, 1 mL formaldehyde, and 100 μl 1N HCl are combined and stirred for 1 hour. The solution is filtered and washed with 10 mL THF and the filtrate is diluted with 100 mL of water and extracted with ethyl acetate. The ethyl acetate phase is washed with brine, dried (MgSO4) and concentrated. The resulting peptide aldehyde can then be purified by C-18 reverse phase HPLC, using an aqueous/acetonitrile (0.1% TFA) system to give the corresponding TFA salts. The crude product was purified using reverse phase high performance chromatography on a 10 micron 300 angstrom pore size C-18 packing. The column was eluted with a aqueous gradient of 0.01% trifluoroacetic acid gradient going from 5% to 60% acetonitrile containing 0.01% trifluoroacetic acid. Lyophilization of the appropriate fractions gave the title compound as its trifluoroacetate salt. FAB mass spectrum: calculated mw=503; obs. mw=503.

What is claimed is:

1. A compound of the formula:

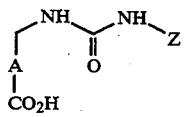

wherein
(a) A is a non-reactive hydrocarbyl group having from 2 to about 15 carbon atoms; and
(b) Z is selected from —NH—Pr; (i)

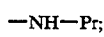

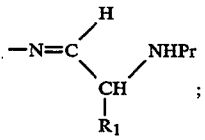

and

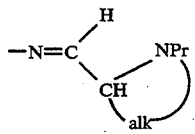

wherein Pr is a protecting group removable under non-adverse conditions and R1 is hydrogen; or alkyl, cycloalkyl, aryl or aralkyl, optionally substituted with 1 to 3 substituents independently selected from hydroxy, alkoxy, sulfhydryl, alkylthio, carboxy, amide, amino, alkylamino, indolyl, 3-N-formylindolyl, benzyloxy, halobenzyloxy, guanido, nitro-guanido or optionally substituted imidazolyl substituted with alkoxyalkyl; and alk is an alkylene group of about 3 to about 12 carbon atoms optionally substituted with 1 to 3 substituents independently selected from hydroxy, alkyl, aryl or guanido; and provided that any functional groups of R1 or alk which are reactive under conditions of peptide synthesis are optionally protected by a protecting group which is removable under non-adverse conditions.

2. A compound according to claim 1 wherein A has from about 5 to about 10 carbon atoms.

3. A compound according to claim 2 wherein Z is —NH—Pr.

4. A compound according to claim 3 wherein A is a divalent radical selected from cycloalkylene, arylene and aralkylene, all having from about 5 to about 8 carbon atoms and optionally substituted with from 1 to 5 alkyl groups.

5. A compound according to claim 2 wherein Z is:

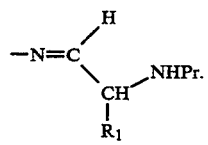

6. A compound according to claim 5 wherein A is a divalent radical selected from cycloalkylene, arylene and aralkylene all having from about 5 to about 8 carbon atoms and optionally substituted from 1 to 5 alkyl groups.

7. A compound according to claim 6 wherein A is 1,4-cyclohexylene, 1,3-cyclohexylene, 1,3-phenylene, or 1,4-phenylene, 1,3-xylylene or 1,4-xylylene.

8. A compound according to claim 7 wherein R1 is hydrogen, alkyl of 1 to 12 carbon atoms, cycloalkyl of about 5 to 8 carbon atoms or aryl or aralkyl of about 5 to 10 carbon atoms, all optionally substituted with a substituent independently selected from hydroxy, alkoxy, carboxy, amino, amidophenyl, phenoxy, guanido, nitroguanido, imidazolyl or indolyl.

9. A compound according to claim 7 wherein R1 is selected from the side chains of glycine, alanine, valine, leucine, isoleucine, serine, threonine, cysteine, methionine, glutamic acid, aspartic acid, glutamine, asparagine, lysine, arginine, histine, phenylalanine, tyrosine and tryptophan.

10. A compound according to claim 9 wherein A is trans-4-methyl-1,4-cyclohexylene, and R1 is the side chain of N$^g$-nitroarginine.

11. A compound according to claim 2 wherein Z is:

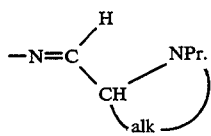

12. A compound according to claim 11 wherein A is a divalent radical selected from cycloalkylene, arylene and aralkylene, all having from about 5 to 8 carbon atoms and optionally substituted with from 1 to 5 alkyl groups.

13. A compound according to claim 12 wherein alk is propylene or hydroxy-propylene.

14. A compound according to claim 13 wherein A is 1,3-cyclohexylene; 1,4-cyclohexylene; 1,3-phenylene or 1,4-phenylene, 1,3-xylylene or 1,4-xylylene.

* * * * *